United States Patent [19]

Crews et al.

[11] Patent Number: 4,947,878

[45] Date of Patent: Aug. 14, 1990

[54] COMPOSITIONS AND METHODS FOR THE TREATMENT OF HAIR

[75] Inventors: Harold R. Crews, Pembroke Pine, Fla.; Roy M. Evans, Jr.; Joseph O. Rubert, both of Memphis, Tenn.

[73] Assignee: Preemptive Marketing, Inc., Memphis, Tenn.

[21] Appl. No.: 27,564

[22] Filed: Mar. 18, 1987

[51] Int. Cl.$^5$ .............................................. A61K 7/09
[52] U.S. Cl. ................................... 132/203; 132/202; 424/71
[58] Field of Search ....................... 132/202, 203, 204; 424/70, 71, 72

[56] References Cited

U.S. PATENT DOCUMENTS 4,764,363  8/1988  Bolich, Jr. ....................... 521/86 X

FOREIGN PATENT DOCUMENTS 2410677  9/1974  Fed. Rep. of Germany ........ 424/71
0139410  10/1981  Japan ..................................... 424/72
2078804  1/1982  United Kingdom .................. 424/71

Primary Examiner—Alan W. Cannon
Attorney, Agent, or Firm—Woodcock Washburn Kurtz Mackiewicz & Norris

[57] ABSTRACT

Disclosed are methods and compositions for the treatment of hair. Treating compositions comprising the amino acid cysteine and a non-reducing disaccharide in solution are disclosed. The methods of the present invention comprise application of the aqueous solution to the hair for permanently altering the natural shape of the hair.

13 Claims, No Drawings

COMPOSITIONS AND METHODS FOR THE TREATMENT OF HAIR

The present invention relates to methods and compositions for the treatment of hair, and more particularly to methods and compositions for permanently altering the natural shape of hair.

It has heretofore been common practice to treat kinky or curly hair with highly alkaline or caustic aqueous solutions, usually sodium hydroxide, calcium hydroxide or ammonium thioglycolate solutions, in an effort to soften or reduce the natural elasticity or resiliency of the hair. While the use of such solutions has been partially effective, there are many serious disadvantages as well. For example, methods employing such compositions usually require that the hair and scalp be exposed to highly caustic conditions (e.g.: pH of about 12 to 14) for extended periods of time (e.g.: 45 minutes). Such exposure frequently has a permanent deleterious effect on the aesthetic and structural qualities of the hair and may frequently cause severe irritation or burning of the scalp. See for example the article by F. Lewis, M.D., in the Journal of the American Medical Association, Jan. 7, 1939. Moreover, such compositions usually have a very unpleasant odor and are uncomfortable to the person whose hair is being treated. Moreover, it is difficult or impossible to alleviate such offensive odors by traditional methods, such as including a pleasant fragrancing agent in the solution since the compounds of the fragrance are usually destroyed or rendered ineffective in highly caustic solutions. Such compositions also appear to cause changes in the structure of the hair which precludes further beneficial chemical treatment of the hair.

Methods are also currently available for imparting a so-called "permanent wave" to hair which is naturally relatively straight. One frequently used method requires application of a highly alkaline solution to the hair and subsequent physical curling of the hair in the presence of heat. See for example U.S. Pat. No. 2,115,156—Brown. In addition to the disadvantages described above in connection with the use of highly caustic solutions, another problem with such methods is that they require the use of high heat in close proximity to the skin and scalp, creating the potential for severe burning.

Methods also exist for imparting a permanent wave to hair without the application of heat. Such methods generally require the application of a highly alkaline softening composition to the hair, followed by mechanically conforming the hair to the desired shape. An acidic fixing composition is then applied directly to the conformed and softened hair. The fixing composition neutralizes the softening composition and is said to restore the natural elasticity to the hair. An example of such a method is described in U.S. Pat. No. 2,061,709—Malone. Once again, these methods suffer from all the disadvantages associated with the application of a highly caustic composition to the hair. Moreover, it is difficult, if not impossible, to apply the exact amount of acidic fixing composition required to completely neutralize the softening composition without leaving the hair in a slightly acid condition, which in turn will result in an undesirable further softening of the hair.

Another method which has heretofore been used for the treatment of hair includes mixing cysteine in powder or crystalline form to a treating solution just prior to application of the solution to the hair. The treating solution of such heretofore used methods generally comprised sodium hydroxide solutions having a pH of about 12. Of course, such caustic solutions suffer from all the disadvantages described above, such as the scalp burning and hair damage which may result from the use thereof. Moreover and just as importantly, cysteine is unstable in aqueous solution and is readily oxidized by dissolved oxygen, thereby precluding long-term storage of the heretofore used solutions. Another disadvantage is that such methods are cumbersome, inconvenient and may result in an improperly formulated treating solution. It also is relatively expensive to separately and anaerobically package an accurately defined amount of cysteine powder, as would be required to prevent oxidation or decomposition.

It is accordingly an object of the present invention to provide methods and compositions for the safe and effective chemical treatment of hair.

It is a further object of the present invention to provide methods and compositions for imparting a permanent wave to hair without the application of substantial heat thereto.

It is a still further object of the present invention to provide methods and compositions for altering the configuration of hair without exposing the hair to highly caustic solutions.

It is another object of the present invention to provide a stable aqueous solution containing cysteine for the treatment of hair.

SUMMARY OF THE INVENTION

According to the present invention, applicants have found that certain stabilized solutions of cysteine are effective softening or reducing agents in the treatment of hair. More particularly, applicants have found that aqueous solutions containing cysteine and a non-reducing disaccharide are stable and effective compositions for treating hair.

The present invention also provides methods for treating hair to obtain a modified hair configuration. In particular, it is preferred that the methods comprise applying a stabilized aqueous solution of cysteine to the hair, placing the hair in the modified configuration, and thereafter oxidizing the hair while it is still in said modified configuration.

DETAILED DESCRIPTION

In order to more fully understand the compositions and methods of the present invention, it is helpful to understand the basic structure of hair. Hair is a complex organic substance consisting largely of the protein keratin. More specifically, hair is a proteinaceous fiber comprising a bundle of long individual protein molecules which are intertwined with one another and cross linked at various intervals. Each individual protein molecule comprises condensed amino acids in which the acid end of one molecule is condensed with the amino end of the next. The amino acids are alike in that they all contain an acid group and an amino group, but they may not be alike in certain other details of the arrangement of their atoms. Hair protein generally contains from about 5% to about 15% by weight of the amino acid cysteine, which has the empirical chemical formula $C_6H_{12}N_2O_4S_2$ and generally conforms to the molecular chemical formula given below:

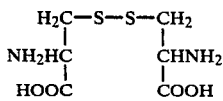

It has been postulated that cystine frequently appears in the fibrous bundle of keratin protein molecules as a bridge between adjacent peptide chains and that it may also frequently appear as a loop or bridge between two segments of the same peptide chain. It is believed that these cystine bridges affect, and in large part determine, the physical shape and conformation of the hair. It has also been postulated that links between adjacent peptide chains may also occur by the ionization of the carboxyl and amino groups to form a salt bridge. Hydrogen bonding is believed to provide a third means by which linkage between adjacent peptide chains may be achieved. It is believed that these additional linkage mechanisms also affect the physical shape and conformation of the hair. See chapter 26 of the book "Chemical and Manufacture of Cosmetics" by Mason G. Denavarre and the first chapter of the book entitled "The Proteins Volume 4", Third Edition, edited by Hans Nuroff and Robert L. Hill, 1979, both which are incorporated herein by reference.

Applicants have found that solutions, preferably aqueous solutions, of cysteine and a non-reducing disaccharide are effective in reductively cleaving the sulfur-sulfur bonds of the cystine bridges in hair, and that such cleavage tends to "soften" the hair. As the term is used herein, "softened hair" refers to hair which has been rendered malleable relative to its natural resiliency. In the compositions of the present invention, cysteine is believed to cause reductive cleavage of at least a portion of the disulfide bonds within and between the individual protein chains which comprise the hair. This cleavage softens the hair and allows the hair to be more readily reconfigured.

Cysteine has the empirical chemical formula $C_3H_7NO_2S$ and the molecular chemical formula given below:

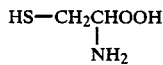

It will be understood that the term cysteine as used herein encompasses within its scope all the various enantiomeric and ionic forms that the cysteine molecule is capable of taking in solution, it being contemplated that all such forms will be capable of performing the desired function. For example, unless otherwise specifically designated herein, the term cysteine includes both L and D enantiomers of that component. Applicant believes that up to the solubility limit of cysteine, all concentrations of cysteine in the softening compositions of the present invention will have a degree of effectiveness and therefore all such concentrations are within the scope of the present invention. It is preferred, however, that the concentration of cysteine range from about 1.0 weight percent to about 20 weight percent, and more preferably from about 6 weight percent to about 14 weight percent, depending upon the pH of the solution. For example, when the solution has a pH of between about 8 and about 10, it is preferred that the cysteine concentration range from about 13 weight percent to about 14 weight percent.

As mentioned above, cysteine is generally very unstable in a solution and is readily oxidized by oxygen which may be dissolved in the solution. This oxidization is manifest in the formation of solid precipitate when an aqueous solution of cysteine is allowed to stand for more than a few hours. Applicant has found that the inclusion of standard anti-oxidants is generally ineffective for stabilizing aqueous solutions of cysteine. In particular, applicant has found that anti-oxidants such as butylated hydroxy toluene (BHT), ascorbic acid, mercaptans, and hydrogen sulfites are generally ineffective in stabilizing aqueous solutions of cysteine. Importantly and surprisingly, however, applicant has found that the inclusion of a non-reducing disaccharide in an aqueous solution of cysteine stabilize the solution and protects the cysteine from oxidization or other degradation. As the term is used herein, a non reducing disaccharide is any disaccharide which does not reduce Fehling's solution. In particular, applicant has found that the use of sucrose is effective and preferred. For example, cysteine solutions containing sucrose according to the present invention have been shown to have at least a one year shelf life.

It has also been found that the inclusion of a non-reducing disaccharide, preferably sucrose, in the compositions of the present invention surprisingly enhances the softening process. While applicant does not intend to be bound by or to any particular theory, it is believed that the disaccharide provides abundant sites for hydrogen bonding with the molecules which make up the hair. The availability of such sites is believed to compete for the otherwise intermolecular hydrogen bonding which is present among the protein strands. This in turn opens the tertiary or spatial structure of the protein fibers, thereby facilitating reduction of the disulfide, cystine, down to the thiol, cysteine.

Applicant believes that the inclusion of a non-reducing disaccharide in any measurable concentration in the composition of the present invention will be effective to a degree in stabilizing the softening solution. That is, applicant has found that the concentration of the sucrose impacts the stabilizing effect in degree only and therefore may be varied over a wide range as desired. In particular, those solutions having relatively low concentrations of the sucrose will tend to provide a shorter shelf life than those solutions having relatively high sucrose concentrations. Moreover, high concentrations of sucrose in the solution may tend to make the softening composition syrupy and more viscous than is desired in certain embodiments. Accordingly, all concentrations of sucrose are within the scope of the present invention. Applicant has found, however, that the concentration of sucrose will preferably range from about 2 weight percent to about 15 weight percent, more preferably from about 4 weight percent to about 12 weight percent, and even more preferably from about 4 weight percent to about 8 weight percent.

Applicants have thus discovered a softening composition, in the form of an aqueous solution, which contains the natural and effective reducing agent cysteine and which has a high degree of stability and a relatively long shelf life. Applicants have found that the inclusion of non reductive disaccharides, e.g. sucrose, is an important characteristic of the compositions of the present invention. Reductive saccharides, such as maltose and lactose, on the other hand, have been found to be generally ineffective, possibly because they compete with the preferred reducing agent of the solution, cysteine. Accordingly, it is preferred that disaccharides which are non-reductive be used in the compositions of the present invention.

It is generally preferred that compositions of the present invention comprise an aqueous solution which is not highly caustic. In particular, it is preferred that the pH of the solution be from about 5 to 12, more preferably from about 7 to 11, and even more preferably from about 8 to 10. Thus, in the more preferred embodiments of the present invention, the pH of the reducing composition is high enough to help break the ionic bridges between adjacent protein molecules and thus to enhance the softening capacity of the composition but is low enough to be safe to the scalp and skin. According to preferred embodiment of the present invention, an alkalizing agent such as ethanolamine is present to adjust the pH of the composition as required. In certain preferred embodiments, ethanolamine is present in a concentration of about 3 weight percent to about 6 weight percent.

According to certain preferred embodiments, the compositions of the present invention further include at least one penetrating agent. As the term is used herein, a penetrating agent is any material which improves penetration of the solutions into the hair. Although any penetrating agent heretofore used for the purpose can be used in the present invention as well, particularly preferred penetrating agents are propylene glycol, monoethanolamine, any ethoxylate group, and oleth-20, the latter being the generic term for the polyethyleneglycol ether of oleyl or laural alcohol having the formula: $CH_3(CH_2)_7CH=CH(CH_2)_7CH_2(OCH_2CH_2)_nOH$, wherein n has an average value of about 20. Oleth-20 is sold under the trade name "BRIJ" by ICI Americas Corp The concentration of the penetrating agents to be used according to the compositions of the present invention will vary greatly depending upon the amount of penetration desired, and accordingly all such concentrations are within the scope of the present invention. Applicant has found that compositions containing a penetrating agent in concentrations from about 4 weight percent to about 10 weight percent are preferred.

In certain embodiments, it is preferred that the compositions of the present invention include chelating agents. As the term is used herein, a chelating agent is any polydentate ligand capable of forming a complex with a metal ion. While many such chelating agents are readily available and well known in the art, common chelating agents include amine containing acids, hydroxy carboxylic acids, dicarboxylic acids, alkali metal salts of the foregoing acids, and mixtures of these. It is preferred that the chelating agent comprise hydroxy ethylenediaminetriacetic acid (hereinafter H-EDTA) and even more preferably alkali metal salts of H-EDTA. It is generally preferred that sodium salts of H-EDTA be used as the chelating agents of the present invention, and it is even more preferred that trisodium salt of H-EDTA is used as the chelating agent. The inclusion of chelating agents in the compositions of the present invention beneficially removes toxic heavy metals, such as mercury, cadmium, and lead, which are otherwise bound to the thio groups of cysteine in the hair protein. Freeing these thio groups is beneficial since they aid in forming the new disulfide linkages after the hair has been reconfigured, thereby helping to maintain the hair in its new configuration. The concentration of the chelating agents according to the compositions of the present invention will vary greatly depending upon the circumstances attendant with its use in each individual case, and accordingly all such concentrations are within the scope of the present invention. Applicant has found however, that chelating agents are preferably included in the compositions of the present invention in concentrations from about 0.25 weight percent to about 1.5 weight percent.

In certain embodiments, it is preferred that the compositions of the present invention also include thickening agents. As the term is used herein, a thickening agent is any agent which provides a high viscosity to the softening solution thus making it easier to apply. Moreover, the relatively high viscosity imparted by the thickening agent enhances uniform spreading of the treating solution and retards dripping and evaporation of the solution. It is preferred that the thickening agent be water soluble so that it may be readily included in the aqueous solutions of the present invention. While many such thickening agents are available and well known in the art, it is preferred that the thickening agent comprise hydroxy ethylcellulose. The concentration of the thickening agents used according to the compositions of the present invention will vary greatly upon the desired result in each individual case, and accordingly all such concentrations are within the scope of the present invention. Applicant has found, however, that thickening agent concentrations of from about 0.5 weight percent to about 2.0 weight percent are preferred.

The present invention also provides methods for modifying the natural conformation of existing hair. As the term is used herein, existing hair refers to fully developed excutaneous hair. As used herein, the term "natural configuration" refers to the configuration of the hair prior to being treated according to the methods of the present invention. That is, the term "natural configuration" is used for convenience only and does not limit the methods of the present invention to treatment of hair which has not been previously treated. Surprisingly and beneficially, the use of the methods and compositions of the present invention provide the capability for effective and nondamaging treatment of previously treated hair. In contrast to the methods and compositions heretofore used, the present invention achieves softening or relaxation of the hair by relatively benign repositioning of the natural constituents of the hair without causing permanent damage thereto. As a result, hair may be subjected to a plurality of treatments without being damaged to any substantial extent.

An important aspect of the methods of the present invention is application of the compositions of the present invention to the hair of the person to be treated. While many methods are known and available to those skilled in the art for the application of softening solutions and those methods may be readily adapted for use with the present compositions, it is preferred that the present compositions be directly applied to the hair. In particular, it is preferred that the application start at the scalp and move progressively outward towards the ends of the hair until the hair being treated is covered thoroughly. It will be understood by those skilled in the art that the particular application method step described above provides unique and substantial advantages over those methods generally used in the prior art. For example, application of the highly alkaline softening compositions heretofore used generally presented a serious risk of caustic burn to both the subject being treated and the person conducting the treatment (hereinafter "the operator"). Accordingly, prior methods require that precautions be taken in order to protect both the user and operator from caustic burn. For example, kits containing such solutions generally include instructions recommending or requiring that the operator wear gloves during the application step and that the skin of the treated person be protected from the solution by thick and highly viscous gels. Due to the low alkalinity and relatively benign nature of the present compositions, such cumbersome and inconvenient precautions are not necessary. Moreover, it is imperative according to the heretofore used methods that the application period be strictly controlled and minimized so as to avoid damage to the scalp and hair of the person being treated. Overexposure of the hair to such highly caustic solutions would generally cause severe and irreversible degradation of the structure of the hair. In comparison, the benign nature and natural constituents of the softening solutions according to the present invention eliminates the criticality of the application period and extends the maximum application period nearly indefinitely, as more fully described below.

As will be appreciated by those skilled in the art, the amount of softening composition to be applied according to the present invention will vary greatly depending upon a host of individual circumstances. For example, the particular type of hair which is to be treated will have a large impact on the amount of composition to be applied. In particular, it is well known that different types of hair have varying degrees of moisture absorbency. Since softening compositions of the present invention preferably comprise an aqueous solution, the ability of the composition to effect hair softening will depend to some extent upon this property of the individual hair. Likewise, the amount of hair to be treated will also determine the application rate of the softening composition. In addition, the extent to which the natural configuration of the hair is to be modified will also impact upon the amount of the composition to be applied. Accordingly, all application rates and amounts are within the scope of the present invention. Applicant has found, however, that based primarily upon considerations of cost and convenience, that the amount of solution to be applied is preferably from about 3 ounces to about 4 ounces and more preferably from about 3.5 ounces to about 4 ounces.

The application period for the compositions of the present invention will also vary widely depending upon a variety of individual circumstances. Importantly and surprisingly, applicant has found that exposure of the hair and scalp to the compositions of the present invention for extended periods of time will not result in any substantial degradation of the hair or cause deleterious effects to the scalp. On the contrary, it is believed that extended exposure of the hair to the compositions of the present invention, especially those compositions having a pH of about 7, may tend to invigorate and revitalize the hair rather than cause the degradation thereof. While applicant does not intend to be bound by or to any particular theory, both cysteine and cystine are naturally occurring amino acids in keratin and therefore it is believed that extended exposure of the hair to compositions of the present invention will tend to replenish these components of the hair. It will also be appreciated by those skilled in the art that very short application periods are also within the scope of the present invention. That is, a very short application period may be desirable when only a modest modification of the natural hair configuration is to be achieved. Accordingly, all application periods are within the scope of the present invention. Applicants have found, however, that based primarily upon convenience considerations, it is preferred to use the following application periods according to the following approximate hair types:

| Hair Type | Approximate Application Period-Minutes |
|---|---|
| Fine Hair | 20 to 25 |
| Medium Hair | 30 to 45 |
| Coarse Hair | 45 to 60 |

Another step according to the methods of the present invention comprises placing the hair in the desired configuration. Many particular techniques are well known and available in the art for placing the hair in a variety of different configurations. Although the placing step of the present invention may take place either before, during or after the application period, it is generally preferred practice when straightening kinky or curly hair to place the hair in the desired configuration only after the application period has expired. That is, the hair will generally not be manipulated during the application period. When the present invention is used in the treatment of hair having a naturally straight configuration, however, it is generally preferred that the hair be placed in the modified configuration either before or during the application of the softening composition of the present invention. It is believed that the details of the procedures used in any particular case to achieve the desired reconfiguration of the hair will be available and well known to those skilled in the art. In applications requiring curling or waving naturally straight hair, for example, it is anticipated that the methods of the present invention will include coiling or wrapping the hair around curlers or rods after the softening agent has bee applied.

The methods of the present invention also include testing the effectiveness of the softening process. In certain preferred embodiments, especially those embodiments for the straightening of kinky or curly hair, the testing step of the present invention includes running a fine tooth comb through the hair and observing the resiliency of the hair. If the comb moves through the hair with the desired degree of resistance, this is an indication that the softening process has had the desired degree of effectiveness. Depending upon the particular hair type, the extent of desired straightening, and other factors, this step may last a few seconds to several minutes.

According to a preferred aspect of the present invention, the methods of the present invention further include the step of oxidizing the hair which has received the softening composition and which has been placed in the new configuration. This oxidation step can comprise exposing the hair to air or oxygen. In certain other preferred embodiments, the hair is oxidized by contacting it with a chemical oxidizing agent or neutralizer. The oxidization step of the present invention "quenches" the activity of the softening composition. That is, by exposing the cysteine solution to oxidation, the capacity of the composition to soften the hair is reduced or eliminated. In this way, the precise amount of softening required can be controlled. The oxidation step also aids in reestablishment of the disulfide cystine bonds which help give the hair its shape. As discussed earlier, application of the softening composition causes cleavage of these disulfide bonds and, on a macroscopic scale, renders the hair relatively malleable. While not intending to be bound by or to any particular theory, applicant believes that such malleability occurs because at least a portion of the individual protein chains which make up the hair are "decoupled" and allowed to more easily move or slide relative to one another when the disulfide bonds are broken. When the hair is thus subject to the stress caused by placing the hair in the desired configuration, this stress is relieved by the movement of the individual protein chains with respect to one another. The oxidation step according to the methods of the present invention allows such disulfide bonds to be reestablished, thus effecting a permanent reconfiguration of the hair. Standard neutralizing agents are available and well known in the art and the use of all such neutralizing agents are accordingly within the scope of the present invention. Applicant has found, however, that it is preferred to select neutralizing agents from the group consisting of hydrogen peroxides and metal bromate salts, preferably potassium and sodium bromates.

Other well known hair treatment steps may be preferably used in conjunction with the method steps described above. For example, in certain preferred embodiments, the hair is shampooed prior to application of the compositions of the present invention. Shampooing in this manner removes fatty acids and oils from the hair and allows enhanced penetration of the softening composition. In a like manner, it may also be preferred to condition the hair prior to the application of the softening composition. In certain embodiments, it is also preferred that the hair be rinsed with tepid water after the application period has expired. In general, the solution which is rinsed from the hair will become clear when the rinsing step is complete. More specifically, the rinsing step is expected to last approximately five minutes. In an analogous manner, it is preferred that the hair is also rinsed after the neutralization step is complete. In order to improve the longevity of the curling and straightening process, applicant has also found that it may be desireable to spray the hair after neutralization with an ammonium sulfite solution.

While applicant believes that many techniques are known and available for effectively producing compositions of the present invention, applicant has found that certain preparation methods are preferred. In particular, it is preferred that cysteine be introduced into solution in the form of hydrated L-cysteine hydrochloride since such material is readily available and contains a relatively precisely known number of milliequivalents of thiol per gram. Due to the acidic nature of hydrated L-cysteine hydrochloride in solution, however, it is preferred that a metal hydroxide be added to the solution during preparation to neutralize the acid component of the L-cysteine hydrochloride. Accordingly, it is preferred that potassium or sodium hydroxide be added to the solution in an amount sufficient to provide the required number of milliequivalents of hydroxide to neutralize the acid component of the L-cysteine hydrochloride. In the methods of the present invention for preparing the softening compositions thereof, it is also preferred to introduce a standard anti-oxidant into solution during the preparation process. Although such anti-oxidants are not generally effective for stabilizing the solution, they are beneficial in that they act as scavengers for the oxygen which is introduced into the solution during the preparation process. Other preferred aspects of the preparation methods according to the present invention are disclosed in the examples which follow.

EXAMPLE 1

In a tank capable of both heating and mixing the contents thereof, (hereinafter tank A), heat 40.82 grams of deionized water to a temperature of between about 60° and 65° C. In a separate tank capable of heating and mixing the contents thereof (hereinafter tank A') introduce 2 grams of propylene glycol. While mixing, add one gram of hydroxyethylcellulose to tank A' and disperse well. Immediately upon dispersion of the hydroxymethylcellulose and prior to substantial hydration thereof, introduce the contents of tank A' into tank A. Continue mixing the contents of tank A for approximately one hour or until hydration is complete. Once hydration is complete, allow the contents of tank A to cool to between about 22° to about 25° C. and then discontinue mixing. Let the contents stand in order to dearate entrapped air. Into a third tank capable of cooling an mixing the content thereof, preferably a 316 stainless steel or fiberglass tank (hereinafter tank B), introduce 20 grams of deionized water. Add 6 grams of sucrose and one gram of trisodium H-EDTA into tank B until completely dissolved. Then add, while mixing, 4.65 grams of potassium hydroxide and 4.1 grams of ethanolamine to tank B and cool the mixture to a temperature of about 25° C. Add 13.13 grams of L-cysteine hydrochloride to the contents of tank B and mix until dissolved. Add, while mixing, one gram of ethanolamine sulfite to the contents of tank B. In a fourth tank having the capability of heating and mixing the contents thereof (hereinafter tank B'), introduce six grams of oleth-20 and heat to about 50° C. Add about 0.3 grams of a fragrancing agent to tank B' and mix well. Introduce the contents of tank B' into tank B and mix until a solution is obtained. Cool tank B to a temperature of between about 22° and about 25° C. Admix 43 grams of the solution contained in tank A and 57 grams of the solution contained in tank B until a uniform solution is obtained. The resulting solution has the following properties and component concentrations:

| Property | Value |
|---|---|
| pH | 9–9.5 |
| Viscosity | 1700 centipoise |
| Shelf life | 1 year |
| Component | Wt. % |
| Water | 60.34 |
| Cysteine.HCl | 13.32 |
| Sucrose | 6.09 |
| Propylene Glycol | 1.96 |
| Hydroxyethyl Cellulose | 1.0 |
| Mono ethanolamine Sulfite | 1.01 |
| Trisodium H-EDTA | 1.01 |
| Oleth-20 | 6.09 |
| Potassium Hydroxide | 4.72 |
| Ethanolamine | 4.16 |
| Fragrance | 0.30 |

What is claimed is:

1. A composition for reductively cleaving the cysteine disulfide bonds of hair to render the hair relatively malleable, said composition comprising an aqueous solution containing from about 6 weight percent to about 14 weight percent cysteine and from about 4 weight percent to about 8 weight percent sucrose, said solution having a pH of from about 8 to about 10.

2. The composition of claim 1 further comprising a penetrating agent

3. The composition of claim 2 wherein said penetrating agent comprises Oleth-20.

4. The composition of claim 1 further comprising a chelating agent.

5. The composition of claim 4 wherein said chelating agent comprises an alkali metal salt of H-EDTA.

6. The composition of claim 4 wherein said chelating agent comprises a trisodium salt of H-EDTA.

7. The composition of claim 1 further comprising a thickening agent.

8. The composition of claim 7 wherein said thickening agent comprises hydroxy ethylcellulose.

9. The composition of claim 1 having a pH of about 7.

10. The composition of claim 9 wherein said solution contains from about 13 weight percent to about 14 weight percent cysteine.

11. The composition of claim 10 wherein said cysteine consists of L-cysteine hydrochloride.

12. The composition of claim 1 wherein said solution comprises L-cysteine hydrochloride in an amount of from about 13 to about 14 weight percent of the solution.

13. The composition of claim 12 wherein said solution has a pH of about 7.

* * * * *

UNITED STATES PATENT AND TRADEMARK OFFICE
CERTIFICATE OF CORRECTION

PATENT NO. : 4,947,878
DATED : August 14, 1990
INVENTOR(S) : Harold R. Crews, Roy M. Evans, Jr., Joseph O. Rubert It is certified that error appears in the above-identified patent and that said Letters Patent is hereby corrected as shown below:

In column 3, lines 44-49, please amend the chemical formula as follows:

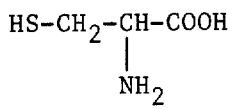

In column 5, line 37, change "Corp" to --Corp.--.

In column 9, line 44, change "desireable" to --desirable--.

Signed and Sealed this

Eighth Day of December, 1992

Attest:

DOUGLAS B. COMER

*Attesting Officer*     *Acting Commissioner of Patents and Trademarks*